US00PP08523P

United States Patent [19]

Trees

[11] Patent Number: Plant 8,523

[45] Date of Patent: Dec. 28, 1993

[54] GERANIUM PLANT 'DESIGNER SALMON'

[75] Inventor: Scott C. Trees, Nipomo, Calif.

[73] Assignee: Ball Floraplant, West Chicago, Ill.

[21] Appl. No.: 996,114

[22] Filed: Dec. 23, 1992

[51] Int. Cl.[5] ..... A01H 5/00

[52] U.S. Cl. ..... Plt./87.12

[58] Field of Search ..... Plt./87.12

[56] References Cited

U.S. PATENT DOCUMENTS

P.P. 5,374 12/1984 Schumann ..... Plt. 87.12
P.P. 5,992 5/1987 Schumann ..... Plt. 87.12
P.P. 7,610 7/1991 Trees ..... Plt. 87.12

*Primary Examiner*—James R. Feyrer
*Attorney, Agent, or Firm*—Arnold, White & Durkee

[57] ABSTRACT

Geranium Designer Series TM Salmon (BFP-165) is a new and distinct cultivar of geranium, botanically known as *Pelargonium* × *hortorum* Bailey, and hereinafter referred to by the cultivar name Designer Salmon. Designer Salmon was selected from among progeny of a cross between female parent Schone Helena and male parent Cabaret. The new cultivar is distinguishable from other geraniums and from both parents in its color and its self-branching without growth regulators.

1 Drawing Sheet

BACKGROUND OF THE NEW PLANT

Designer Salmon is a product of a planned breeding program which had the objective of creating new geranium cultivars with medium green zoned foliage, compact basal branching habit not requiring growth regulators, weather tolerance, floriforous, fast rooting and durable for shipping.

Designer Salmon was originated from a hybridization made in a controlled breeding program in West Chicago, Ill. The female parent was Schone Helena (U.S. Plant Pat. No. 5,374), having a semi-double, medium salmon color flower and medium green foliage. The male parent of Designer Salmon was Cabaret (U.S. Plant Pat. No. 5,992), a plant with a semi-double coral flower and dark green foliage. Cabaret is a dark foliage variety compared to the medium green foliage of Designer Salmon. Cabaret has poor basal branching habit (1–2 branches in a 10 cm pot) compared to Designer Salmon which has 2–3 branches in a 10 cm pot without use of pinching or growth regulators.

Designer Salmon was discovered and selected as one flowering plant within the progeny of the stated cross by the inventor in a controlled environment in Santa Maria, Calif.

The first act of asexual reproduction of Designer Salmon was accomplished when vegetative cuttings were taken from the initial selection in a controlled environment in Santa Maria, Calif. by a technician working under the supervision of the inventor. Horticultural examination of selected units demonstrated that the combination of characteristics as herein disclosed for Designer Salmon are firmly fixed and are retained through successive generations of asexual reproduction.

Designer Salmon has not been observed under all possible environmental conditions. The phenotype may vary significantly with variations in environment such as temperature, light intensity, and day length. The following observations, measurements and comparisons describe plants grown in Arroyo Grande, Calif. under greenhouse conditions which approximate those generally used in commercial practice.

The following traits have been repeatedly observed and are determined to be basic characteristics of Designer Salmon which in combination distinguish this geranium as a new and distinct cultivar. No growth regulators are required for self-branching characteristics. The days to first flower from an unrooted cutting are about 49 days; plant height at first flower is about 23 cm and the plant width at first flower is about 28 cm.

Of the many commercial cultivars known to the present inventor, the most similar in comparison to BFP-65 is Salmon Satisfaction (U.S. Plant Pat. No. 7,610). Designer Salmon is distinctly different in color from Salmon Satisfaction. Both are generally salmon, but the tonality of BFP-165 observed from the same distance of 3 meters is 48C compared to 52C under The Royal Horticultural Society color standards. BFP-165 has more umbels per plant but fewer flowers per umbel than Salmon Satisfaction. BFP-165 has an approximate 4-day shorter spring flower response period and exhibits a self-branching mounded habit compared with the spreading mounded habit for Salmon Satisfaction. In general, there are several other differences between the two plants, BFP-165 being earlier to flower, taller plant at first flower, wider plant at first flower and with less leaf zone than Salmon Satisfaction.

Additionally, there are the following differences between Designer Salmon and Salmon Satisfaction.

(1) Designer Salmon has fewer (1–2) petaloids compared to Salmon Satisfaction which averages 2–3 petaloids. Petaloids are generally large in Designer Salmon and lie flatter against the 5 imbricate petals and petaloids, leading to a more double appearance.

(2) Designer Salmon branches freely without pinching or chemical growth regulators. Designer Salmon has 2–3 branches in a 10 cm pot compared to Salmon Satisfaction which has 1–1.5 branches in a 10 cm pot.

(3) Designer Salmon has thick, sturdy peduncles which withstand wind and rain better than the weaker, thinner peduncles of Salmon Satisfaction.

(4) The flowers (umbels) of Designer Salmon are more tolerant/resistant to Botrytis than those of Salmon Satisfaction.

(5) After boxing cuttings for simulated shipping, the chlorophyll of Designer Salmon does not break down as rapidly as that of Salmon Satisfaction.

(6) Internode length of Designer Salmon ranges from 1.0–1.5 cm compared to 1.0–1.3 cm for Salmon Satisfaction.

(7) Foliage color is different. Designer Salmon has two distinct colors of green in the leaf (137A leaf margin, 137B leaf base) which are lighter than exhibited by Salmon Satisfaction (139A leaf margin, 139C leaf base).

DESCRIPTION OF THE PHOTOGRAPH

The accompanying color photographs show a top view of typical flower and foliage characteristics of Designer Salmon. The view taken against a dark background illustrates flower color closest to the color values assigned from The Royal Horticultural Society Color Chart. The view taken against a light background highlights the leaf characteristics.

DESCRIPTION OF THE PLANT

In the following description, color references are made to The Royal Horticultural Society Color Chart. The color values were determined between 2:00–3:00 p.m. on Nov. 9, 1992 under 700 foot candles at Arroyo Grande, Calif. USA.

Classification:

*Botanical.*—*Pelargonium* × *hortorum* Bailey.

*Commercial.*—Designer Salmon, Zonal Geranium.

INFLORESCENCE

Umbel:

*Average diameter.*—8.5–9.0 cm.

*Average depth.*—7.0–7.5 cm.

*Peduncle length.*—11.0–11.5 cm.

*Pedicel length.*—24–26 mm.

*Number umbels/plant (designate circumstances)*-.—17–19 on 18 week old field grown plant.

*Number of flowers/umbel.*—23–25.

Corolla:

*Average diameter.*—4.3 cm.

*Form.*—Semi-double with petaloids.

*Petal size.*—length: 2.3–2.5 cm; width: 2.3–2.6 cm.

*Number of petaloids.*—1–2.

*Color (General tonality from a distance of three meters).*—Salmon — 48C.

*Description of petal form.*—5–6 Imbricate petals.

*Color (abaxial).*—48C.

*Color (adaxial).*—48D.

*Color stability.*—stable in full sun.

Bud:

*Shape.*—Long-oval.

*Color (abaxial).*—48C.

*Color (adaxial).*—49C.

Reproductive organs:

*Androecium.*—Six 6–8 mm anther/filaments; 22 mm anther.

*Gynoecium.*—8 mm, 5 lobed stigma, 3 mm style.

*Presence or absence of fruits.*—Occasional fruit set.

Spring flowering response period: Designer Salmon is 48.8 days from direct stick, unrooted cuttings.

Outdoor flower production: Designer Salmon averages 17–19 umbels per plant on 18 week old plants, floriforous, continuous.

Durability: Generally more rain and wind tolerant than Salmon Satisfaction.

Foliage:

*Form.*—Reniform, cordate.

*Margin.*—Slightly crenate.

*Color (abaxial).*—137A — leaf margin; 137B — leaf base.

*Color (adaxial).*—147B.

*Color (zonation).*—Slight.

*Tolerance of botrytis.*—None observed.

*Size.*—8.0–9.5 cm at widest point; 4.5–5.5 cm at narrowest point for mature foliage.

*Leaf stems.*—7.8–8.5 cm (mature foliage).

General appearance and form:

*Internode length.*—1–1.5 cm.

*Branching pattern.*—Self branching mounded habit.

*Height.*—22.8 cm tall in 10 cm pot at first flower in during March 1992 trials.

What is claimed is:

1. A new and distinct geranium cultivar, substantially as herein described and shown, characterized by semi-double pink-salmon flowers with petaloids and by self-branching in the absence of growth regulators.

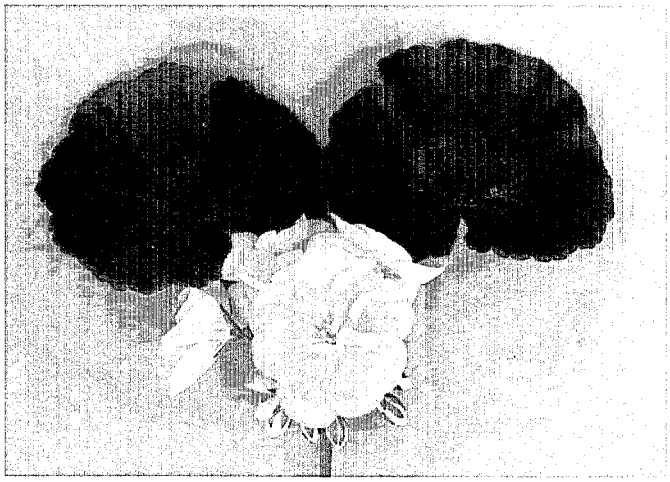
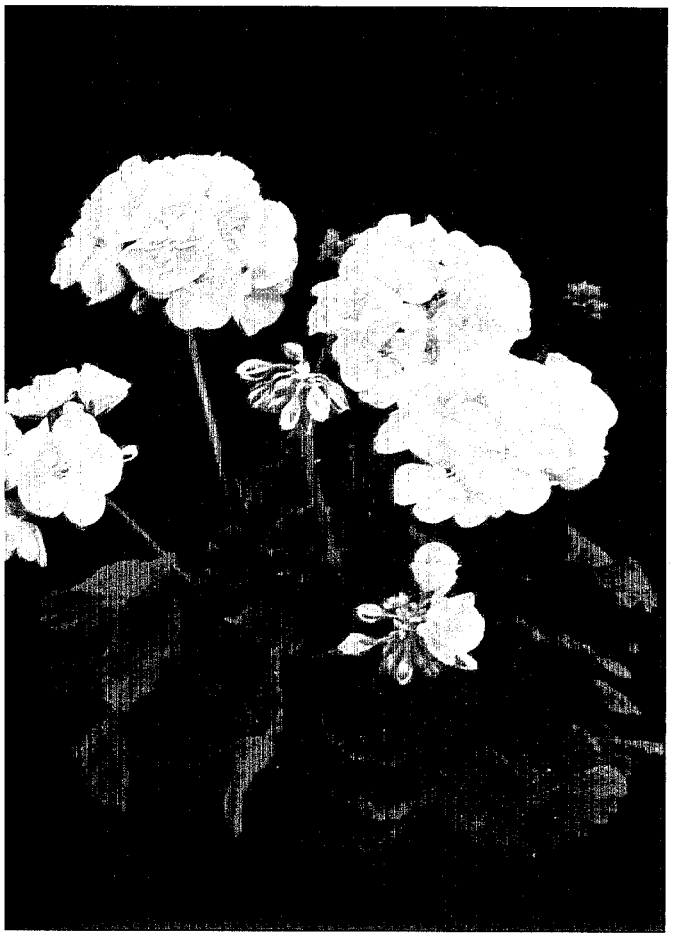

* * * * *